US00PP18671P3

(12) United States Plant Patent
Bol

(10) Patent No.: US PP18,671 P3
(45) Date of Patent: Mar. 25, 2008

(54) ***VERBASCUM* PLANT NAMED 'JACKIE IN SPOTS'**

(50) Latin Name: ***Verbascum* hybrid**
Varietal Denomination: Jackie In Spots

(76) Inventor: Gerrit H. Bol, Katwijkerweg 96, Valkenburg, ZH (NL), 2235 AD ( * ) Notice: Subject to any disclaimer, the term of this patent is extended or adjusted under 35 U.S.C. 154(b) by 0 days.

(21) Appl. No.: 11/471,107

(22) Filed: Jun. 19, 2006

(65) Prior Publication Data

US 2007/0294796 P1 Dec. 20, 2007

(51) Int. Cl.
*A01H 5/00* (2006.01)

(52) U.S. Cl. ..... Plt./263

(58) Field of Classification Search ..... Plt./263
See application file for complete search history.

(56) References Cited

PUBLICATIONS

UPOV–ROM GTITM Plant Variety Database, Jan. 2001, GTI Jouve Retrieval Software, Citation for Verbascum 'Jacky in Spots'one page.*

* cited by examiner

*Primary Examiner*—Kent Bell
*Assistant Examiner*—June Hwu
(74) *Attorney, Agent, or Firm*—Penny J. Aguirre

(57) ABSTRACT

A new cultivar of hybrid *Verbascum,* 'Jackie in Spots', characterized by its creamy white flowers that are blushed with pink margins with red-purple center, its pubescent grey-green foliage, its compact growth habit, and its long blooming habit.

2 Drawing Sheets

Botanical classification: *Verbascum* hybrid.
Cultivar designation: 'Jackie In Spots'.

BACKGROUND OF THE INVENTION

The present invention relates to a new and distinct cultivar of hybrid *Verbascum* plant, botanically known as *Verbascum* 'Jackie in Spots' and will be referred to hereafter by its cultivar name, 'Jackie in Spots'. The new cultivar represents a new Mullein, an herbaceous perennial grown for landscape use.

The inventor discovered the new cultivar, 'Jackie in Spots', in a cultivated growing area at his nursery in Valkenburg, The Netherlands in the summer of 2002. 'Jackie in Spots' originated as a naturally occurring chimeral mutation of *Verbascum* 'Jackie in Pink' (U.S. Plant Pat. No. 15,735).

Asexual reproduction of the new cultivar was first accomplished by in vitro propagation in Noordwijk, The Netherlands in August of 2003 under the direction of the inventor. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Jackie in Spots' from other varieties of *Verbascum* known to the inventor.

1. Flowers are creamy white in color with red purple centers. The petal margins and tips are blushed with red-purple.
2. Exhibits grey-green foliage with a pronounced pubescent surface imparting a silvery appearance.

3. Reaches a compact height of 46 cm and a spread of about 31 cm at maturity.
4. Long blooming; blooms from May to late August in temperate climates.

'Jackie in Spots' differs from the parent plant, 'Jackie in Pink', primarily in flower color as the flowers of 'Jackie in Pink' are pale pink with red-purple centers. 'Jackie in Spots' differs from the cultivar 'Rosie' (U.S. Pat. No. 14,167) in that the flowers of 'Jackie in Spots' are white versus pink in color, and similarly to 'Jackie in Pink', the foliage is more pubescent, and the growth habit is more compact (less spreading).

BRIEF DESCRIPTION OF THE DRAWING

The accompanying colored photographs illustrate the overall appearance and distinct characteristics of the new *Verbascum.*

The photograph in FIG. 1 is a view of a plant of 'Jackie in Spots' in bloom in September as grown in a one-gallon container.

Figure 1:
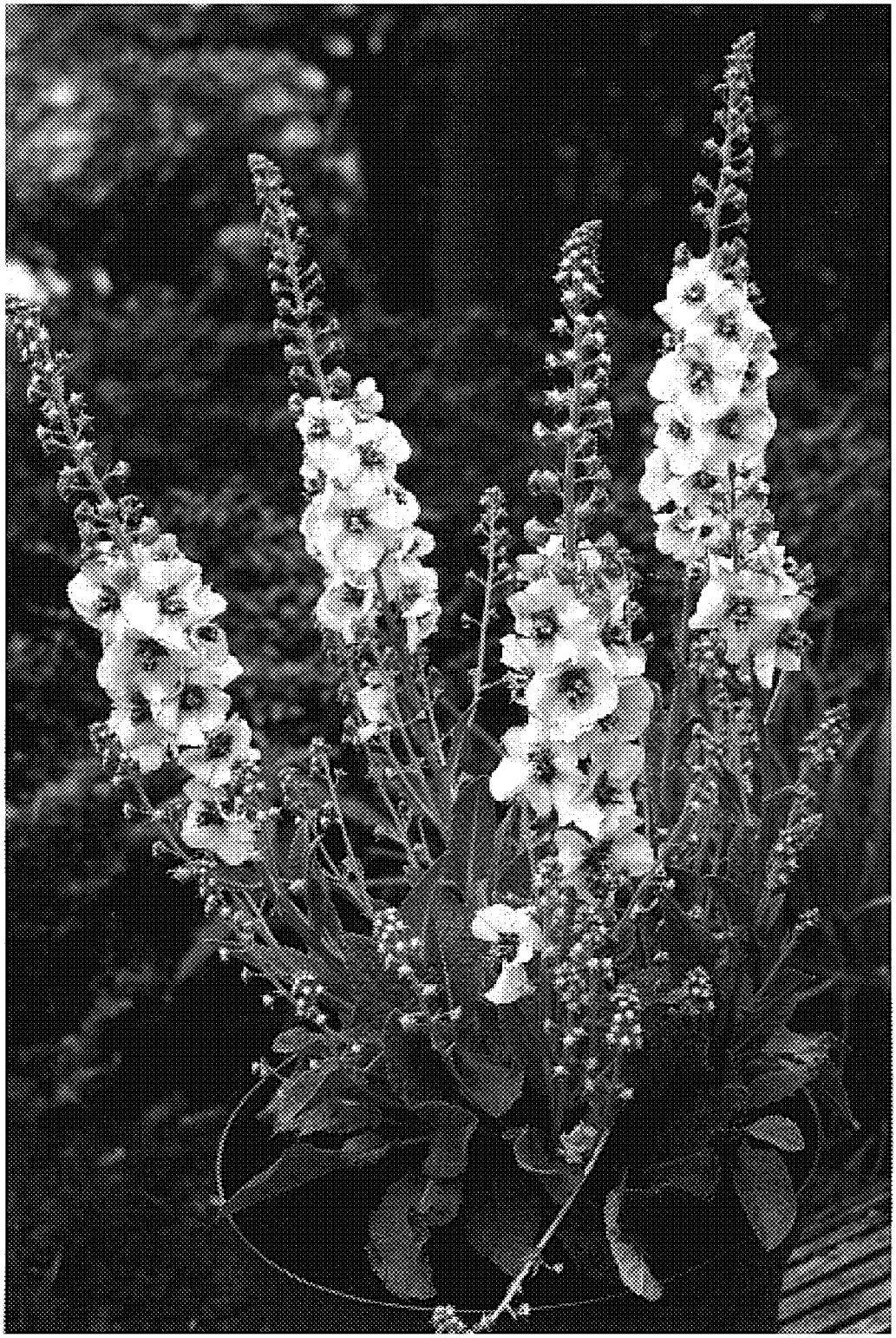
Figure 2:
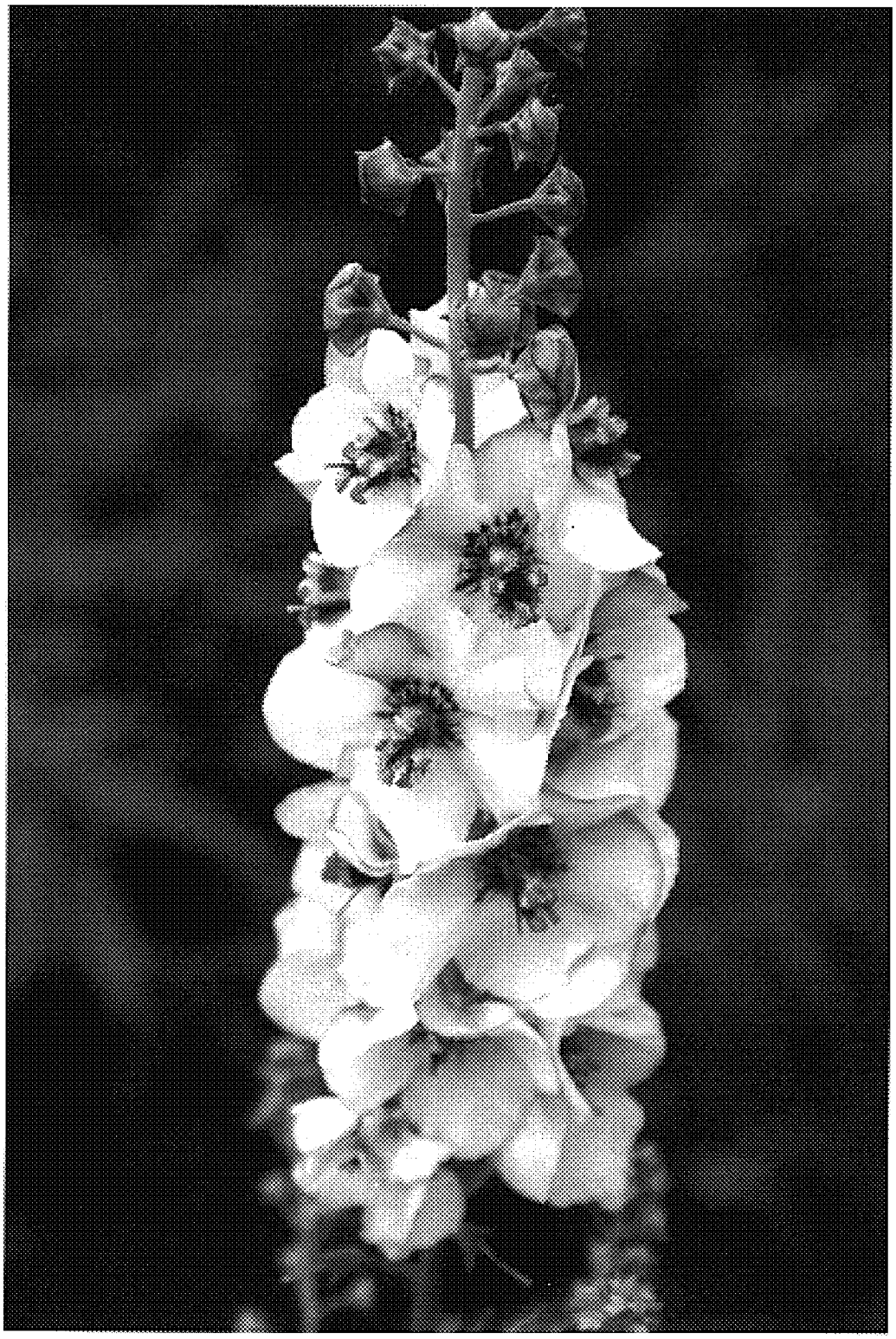

The photograph in FIG. 2 is of a close-up view of the flowers of 'Jackie in Spots'.

The colors in the photographs are as close as possible with the photographic and printing technology utilized. The color values cited in the detailed botanical description accurately describe the colors of the new *Verbascum.*

DETAILED BOTANICAL DESCRIPTION OF THE PLANT

The following is a detailed description of 2 year-old plants of the new cultivar as field grown under natural light in Valkenburg, The Netherlands. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

Botanical classification: 'Jackie in Spots' is a cultivar of *Verbascum* of hybrid origin.

Parentage: Naturally occurring chimeral mutation of *Verbascum* 'Jackie in Pink'.

General description:

*Blooming period.*—May through late August in temperate climates.

*Plant habit.*—Herbaceous perennial, clump-forming, upright flower scapes arise from a rosette of basal foliage.

*Height and spread.*—Reaches about 31 cm in width and about 46 cm in height.

*Hardiness.*—Cold hardy to at least USDA Zone 6, tolerant to a high temperature of at least 30° C.

*Culture.*—Grows best in full sun in alkaline, very well-drained soils of low fertility.

*Diseases and pests.*—No susceptibility or resistance to diseases or pests has been observed.

*Root description.*—Fibrous.

Growth and propagation:

*Propagation.*—In vitro propagation is the preferred method, division are also possible.

*Time required for root development.*—8 weeks to fully develop in a 32 cell in soil-less media when grown at 70-80° F. in a greenhouse without supplemental lighting from a rooted plantlet from tissue culture. A 32-cell plug will fully develop to flowering size grown outdoors under natural lighting in about 15 weeks in a one-gallon container or in the field. Fall, winter and spring are preferred for root development.

*Growth rate.*—Slow to moderate, grows about 8 cm per month in spring.

Stem description:

*Stem size.*—About 1.5 to 3.0 cm in length, 3 to 5 mm in width, appearance is stemless as foliage is arranged in a basal rosette on short, branchless stems.

*Stem shape.*—Round.

*Stem color.*—144A to 144B.

*Stem surface.*—Dull, villous with light green-white (too fine for color code) branched hairs about 0.5 mm in length.

*Branching.*—Basal foliage only.

Foliage description:

*Leaf shape.*—Ovate to narrowly ovate.

*Leaf division.*—Simple.

*Leaf base.*—Rounded on basal leaves and attenuate on stem leaves.

*Leaf apex.*—Rounded to acute.

*Leaf venation.*—Pinnate pattern, color 145C on upper surface and lower surface, raised on lower surface.

*Leaf margins.*—Crenate (average of 4 teeth per cm).

*Leaf attachment.*—Sessile on stem leaves, petiolate on scape leaves.

*Leaf arrangement.*—Basal foliage; rosette, flower scapes; alternate.

*Leaf surface.*—Upper and lower surface; slightly rugose and pubescent with hairs about 0.3 mm in length.

*Leaf color.*—Young: 137A to 137B on upper surface and 137C on lower surface, mature; upper surface 137A and lower surface 137B to 137C.

*Leaf size.*—Basal leaves; average of 9.1 cm in length and 4.5 cm in width, flower scape leaves; average of 5.5 cm in length and 2.7 cm in width.

*Leaf quantity.*—Average of 5 basal leaves and 8 scape leaves per stem.

*Leaf durability to stress.*—High.

*Petioles.*—Average of 2.8 cm in length and an average of 4.5 mm and 3 mm in width (oval in shape), 144C to 144D in color, surface is glabrous.

Flower description:

*Inflorescence type.*—Racemes on flower scapes arising from basal foliage.

*Lastingness of inflorescence.*—Indeterminate, each flower last about 5 days, self-cleaning.

*Size of inflorescence.*—Average of 26.1 cm in height (from lowest flower to apex) and an average of 5.5 cm in width.

*Flower scapes.*—Average of 5 main scapes and 8 lateral stems per main scape, length of main scape is up to 31 cm with an average width of 3.5 mm, length of lateral scapes is an average of 13.4 cm with an average width of 2.5 mm.

*Flower size.*—Average of 1.3 cm in depth and 3.9 cm in diameter.

*Flower fragrance.*—None.

*Flower number.*—About 75 per flowering stem (includes lateral scapes) at one time but new flowers are continuously formed from the apex throughout the summer.

*Flower buds.*—About 6 mm in length and 1 cm in diameter, flattened pentagonal in shape, 182C in color with 64A at the margins of the petals.

*Flower type.*—Rotate, symmetrical, perfect, outward facing.

*Calyx.*—Deeply 5 parted, sepals united at base and spreading when flower opens, average of 7 mm in length and 1.3 cm in diameter, 143A in color, slightly pubescent surface.

*Sepals.*—5, narrowly lanceolate in shape, average of 7 mm in length and 2 mm in width with attenuating to apex, surface is dull with lower surface densely covered with glandular hairs<0.2 mm in length, light orange in color (too fine to color code), entire margins, acute apex, broadly cuneate base, 143A in color on upper surface and 143A in color on lower surface becoming 143B towards base.

*Corolla features.*—Petals distinct but fused at base to a short tube (lower 15%) that is 5 mm in length, and 144D in color, petals overlap near the proximal region, petals broadly flaring with reflexed edges creating a wavy appearance.

*Petals.*—5, orbicular in shape, average of 2 cm in length and 2.3 cm in width, apex is rounded to reniform, margin is entire and sinuate, surface is glabrous and smooth, color opening upper surface; between 158D and 11D with margins and tips flushed with a color lighter than 70C and a base of 60D, color opening lower surface; 158D with margins with a color lighter than 70C, color fully open upper surface; 155C, margins and tips flushed with 70B and N74C, a base of 60C and the main vein flushed 8C near the change from red-purple to white, color fully open lower surface; 155A to 155C, margins and areas of 70C and N74D but lighter.

*Peduncle.*—Strong, held upright on main stem and at an average of 20° from scape on lateral scapes, up to 31 cm in length and an average of 3 mm in diameter, 144B in color, surface is villous on basal region becoming glabrous towards apex, internodes between flowers about 5 mm to 1.7 cm.

*Pedicel.*—Strong, average of 1.3 cm in length and 1 mm in width, held at about 80° from upright, 143B in color, surface is glabrous.

*Bracts.*—Present at the base of each flower, linear in shape, average of 9 mm in length and 3 mm in width, both surfaces are 143B in color and densely covered with very short (<2 mm in length) hairs that are light orange and too fine to color code.

Reproductive organs:

*Gynoecium.*—1 Pistil, about 1.1 cm in length and 1 mm in width; style is N170B in color, stigma is club-shaped and N144B in color, style is about 1 cm in length and N170B in color, ovary is superior and 143C in color.

*Androecium.*—5 stamens, about 2 mm in width and 9 mm in length, filament is N79B to 158C in color and covered with short hairs, anther is N25B in color, dorsifixed and broad triangular, pollen quantity is moderate and 25A in color.

*Fruit.*—No fruit or seeds have been observed under the conditions tested.

I claim:

1. A new and distinct cultivar of *Verbascum* plant named 'Jackie In Spots' as herein illustrated and described.

* * * * *